United States Patent [19]

Morris

[11] 4,377,708

[45] Mar. 22, 1983

[54] HYDROCARBOXYLATION OF VINYL ALKANOATES

[75] Inventor: Donald E. Morris, Kirkwood, Mo.

[73] Assignee: Monsanto Company, St. Louis, Mo.

[21] Appl. No.: 842,438

[22] Filed: Oct. 14, 1977

[51] Int. Cl.$^3$ .................. C07C 51/14; C07C 59/08; C07C 67/38; C07C 69/14

[52] U.S. Cl. .................. 560/266; 260/410.9 R; 260/413; 560/179; 560/232; 560/263; 562/517; 562/589; 562/606; 562/607; 568/450; 568/484

[58] Field of Search .................. 560/266, 232, 233; 260/410.9 R, 4 B; 562/589, 517

[56] References Cited

U.S. PATENT DOCUMENTS

| | | | |
|---|---|---|---|
| 3,437,676 | 4/1969 | Kutepow et al. | 260/532 |
| 3,839,378 | 10/1974 | Yamaguchi et al. | 560/233 |
| 4,072,709 | 2/1978 | Tinker | 560/266 |

Primary Examiner—Vivian Garner

[57] ABSTRACT

Vinyl esters such as vinyl acetate are hydrocarboxylated with tertiary organo-phosphine stabilized palladium catalysts utilizing low water concentration; the ready hydrolysis of the α-acetoxypropionic acid affords a convenient route to lactic acid.

18 Claims, No Drawings

HYDROCARBOXYLATION OF VINYL ALKANOATES

BACKGROUND OF THE INVENTION

The present invention relates to a process for hydrocarboxylating vinyl acetate to produce α-acetoxypropionic acid and ultimately lactic acid.

It is known that carboxylic acids are produced by reaction of olefins with carbon monoxide and water in the presence of various Group VIII metal catalyst systems, notably iodide promoted iridium and rhodium catalysts, as well as some palladium catalysts such as the palladium halide phosphine complexes disclosed in U.S. Pat. No. 3,437,676 and the phosphine stabilized platinum or palladium complexes disclosed in U.S. Pat. No. 3,887,595. However in general such procedures are primarily concerned with hydrocarboxylation of olefinic hydrocarbons or unsaturated compounds containing only non-reactive or non-interfering moieties and involve aspects (procedures) not suitable for hydrocarboxylation of reactive olefins such as vinyl acetate.

SUMMARY OF THE INVENTION

It has now been found that vinyl acetate can be hydrocarboxylated with good selectivity to α-acetoxypropionic acid by reacting the vinyl acetate with carbon monoxide and water in the presence of a phosphine-stabilized palladium catalyst, and with only small concentrations of water being present in the reaction medium. The invention utilizes palladium phosphine complexes in which the palladium is complexed with tertiary organophosphine ligands and additional ligand is provided so that about 10 moles to 150 moles of ligand are provided per atom of palladium. The process can employ mild temperatures, of about 100° to 150° C. or so and uses low concentrations of water, generally no more than 3% by weight of the reaction medium. Additional water is pumped to the reactor as the reaction proceeds. The invention also includes the corresponding hydrocarboxylation of other vinyl alkanoates, particularly of alkanoic acids of up to 6 carbon atoms, to obtain the corresponding α-acyloxy propionic acids. It has further been found that the described hydrocarboxylation together with hydrolysis provides a convenient route to convert vinyl alkanoates to lactic acid either via a one or two-step process. Lactic acid is widely used as a food ingredient and an efficient process for preparing lactic acid from readily available starting materials is desirable.

DETAILED DESCRIPTION OF THE INVENTION

The invention is primarily concerned with hydrocarboxylation of vinyl acetate to α-acetoxypropionic acid, but other vinyl alkanoates can be hydrocarboxylated to the corresponding α-acyloxypropionates in accordance with the procedures herein, e.g. vinyl propionate, vinyl butyrate, vinyl hexanoate, etc. can be hydrocarboxylated by the described procedures. The invention is further concerned with hydrolyzing the α-acyloxypropionic acids to lactic acid and a complete process for converting vinyl acetate to lactic acid. Under some conditions the hydrocarboxylation and hydrolysis can be performed simultaneously, i.e., in the same reaction medium without catalyst separation, to yield lactic acid in one step.

The catalysts utilized herein for hydrocarboxylation are tertiary organophosphine-stabilized palladium complexes, which are used in the presence of a large excess of phosphine. In general any stabilizing tertiary organophosphine ligands can be employed which provide a sufficiently stable catalyst with desirable activity in appropriate temperature ranges, e.g. at relatively mild temperatures up to about 150° C. or so, such as about 100° C. to about 150° C. Tertiary organophosphines of the general formula

are used in which each R is an organo group, ordinarily having no more than 20 carbon atoms. R often is hydrocarbyl with no unsaturation other than aromatic unsaturation, but non-interfering substituents are not precluded, and in fact phosphine stabilized palladium catalysts containing such substituents are known in the art, particularly sulfur, oxygen, nitrogen and halogen. In general it will be preferred to employ tri-aryl phosphines as ligands, as these phosphines tend to provide a more stable and reactive catalyst system, but one or more alkyl or aralkyl groups can be employed on the phosphorus. The R groups on the phosphorus can be the same, or different, but will usually be the same for convenience in preparation. Phosphines with three aromatic groups are the preferred ligand, such as triphenyl or substituted triphenyl phosphines, provided the substituents do not deactivate the catalyst. Other aryl groups including alkyl substituted phenyls can be employed in triarylphosphines, for example tolyl groups, particularly the p- and m-tolyl, as the orthotolyl palladium is prone to decomposition. Tris-(p-fluorophenyl) phosphine is a suitable ligand, but catalyst activities tend to be lower than with triphenyl phosphine. Alkyldiarylphosphines can be employed, e.g. methyldiphenylphosphine, as well as dialkylarylphosphines. Triarylphosphines are preferred as ligands herein. The phosphine stabilized catalysts can be represented by the formula

wherein R has the meaning above and n is a number from 1 to 4. Ordinarily the bulk of the palladium in the complex is in the zero valent state, often as PdL4 where L is a ligand such as triphenylphosphine, but the palladium may cycle between various forms during the reaction, at times being in the palladium (II) state. Moreover, the palladium is often conveniently added to the reaction medium in salt form and subsequently converted to PdL4 and some of the intermediate forms may be catalytic or influence the activity of the catalyst. Initial catalyst forms which can be used for introducing the palladium include, for example,

Pd(acetylacetonate)2, [(alkyl)PdCl]2, PdCl2(triphenylphosphine)2, and Pd(triphenylphosphine)4. The complexes may at times involve dimeric or other forms of complexes involving more than one atom of palladium. Phosphines are utilized for stabilizing purposes in the catalysts used herein, but are not necessarily the only ligands present in the catalysts. Thus sufficient stabilization may possibly be achieved with other ligands present along with the phosphine, in the presence of the large excess of phosphine utilized herein. The palladium forms used herein are characteristically converted almost completely to $PdL_4$ in the course of the hydrocarboxylation reaction, but this is not always the case, as some palladium compounds relatively resistant to reduction to $PdL_4$ are still effective as catalysts herein. The ligand L, is generally $R_3P$. However, in some cases, all or part of the L may be CO, and the catalyst can be represented:

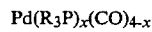

$Pd(R_3P)_x(CO)_{4-x}$

The palladium catalysts are phosphine-stabilized, regardless of the particular form, as a large excess of phosphine is present during the present process. Thus the amount of phosphine in the reaction medium is from about 10 moles up to about 150 moles or more per atom of palladium, and preferably about 15 to about 30 moles on such basis. The phosphine employed in excess will generally be the same as that present as ligands in the catalysts, but mixtures of phosphines can be used if desired. Sufficient phosphine should be present to achieve the desired stabilizing effect and activity, which usually means at least about 10 moles per atom of palladium. However extremely high concentrations of phosphine tend to promote side reactions, thereby lowering selectivity to the desired α-acetoxypropionic acid. A balance of desired effects can be obtained by utilizing about 20 moles phosphine per atom of palladium.

It will be recognized that catalysts are subject to deterioration upon use or recycling, and reference herein to stabilization of the catalyst does not mean that the catalysts are free from such deterioration. The stabilized catalysts utilized herein will have sufficient stability under the reaction conditions to effect the hydrocarboxylation, but this does not necessarily mean they will be characterized by long-life, and the lives of particular catalysts may vary considerably.

In hydrocarboxylations of unsaturated olefinic hydrocarbons over various nobel metal catalysts, it has often been found that arsines, stibines, phosphites, etc. can be used as catalyst ligands with effects similar to phosphine ligands. However in the hydrocarboxylation process of the present invention, such other ligands have not been found effective.

General conditions and procedures for conducting hydrocarboxylations are known in the art and can be adapted or modified to meet the particular requirements of the present process in accordance with the teaching herein. The present process can be effected under relatively mild conditions in view of the fairly good activity of the catalysts under such conditions. This is particularly significant in the present process since it involves vinyl acetate as reactant, and vinyl acetate is amenable to a number of reactions other than the desired hydrocarboxylation, and such undesired reactions are in general favored by high temperature. Thus vinyl acetate in the presence of water can be hydrolyzed to vinyl alcohol and acetic acid, and the vinyl alcohol can rearrange to acetaldehyde. Mild temperatures may also have an influence on directing the reaction to the desired carbonylation on the α-carbon of the vinyl acetate, rather than to some involvement of the β-carbon followed by decomposition or other reactions producing undesired products. Extremely high pressures are not required in the present process which can conveniently be operated at say 100 to 1000 psi gauge. However higher pressures can be employed up to 1000 or more atmospheres, so appropriate conditions can be employed from relatively mild pressure or a few atmospheres up to 1000 to more atmospheres.

It is one of the advantages of the present process that relatively mild temperatures are effective, such as 100° C. to 150° to 170° C. However higher temperatures can be employed with some success, up to 200° C. or even higher, although the tendency toward undesired side reactions increases greatly with increases in temperature in such higher ranges.

Water is a reactant in the present process and therefore its presence is required. However, as vinyl acetate is not a simple olefin but contains a hydrolyzable group, a site is provided for an undesired competing reaction with the water. To have good selectivity to the desired α-acetoxypropionic acid, it is necessary to have conditions favoring the desired hydrocarboxylation at the expense of undesired hydrolysis and rearrangement reactions. In the present process high concentrations of water are avoided in order to favor the desired hydrocarboxylation. Water, of course, must be provided at some stage in sufficient amount to take part in the reaction, requiring one mole of water for each mole of vinyl acetate carboxylated. However, much less than stoichiometric amounts can be present during the course of the reaction, with continuous or incremental addition to provide the necessary amount as the reaction proceeds. In the ordinary operation of the process, the concentration of water is kept low, no greater than about 3% by weight of the reaction medium, and additional water added as needed to replace that reacted. In batch reactions, for example, the vinyl acetate is present initially along with solvent and slightly less than 1% water, and the reaction is conducted under carbon monoxide pressure at 100°–150° C. or so, with additional water being added over several hours as needed to replenish that consumed in the reaction. The reaction can be monitored by the CO uptake (pressure measurement) to determine water needed, with one mole water being needed for each mole of carbon monoxide, according to reaction stoichiometry. During the early stages of a batch reaction, the vinyl acetate will be present in large excess over the water, and the amount of water will ordinarily approach the stoichiometric amount only as the conversion of vinyl acetate approaches 100%. However, aside from such ratios, having only a small concentration of water present tends to limit the amount of hydrolytic or related side reactions. In continuous reactions, as in a flowing stream etc., water can be added at various locations or other procedures can be adapted to avoid high water concentrations. The ratios of water to vinyl acetate may in some instances in such procedures vary from those prevailing in usual batch reactions, so long as the water is not supplied in a way to have a substantial excess of water over that taking part in the hydrocarboxylation reaction. Thus one aspect of the present invention involves supplying water for the reaction at the rate it is utilized in hydrocarboxylation. It will be recognized, of course, that this is an approximation, as some water will take part in side reactions, and there are some limits on how precisely the reaction can be monitored.

The catalysts utilized in the present invention function without requiring a halide promoter. Thus iridium and rhodium catalysts promoted by excess iodide, which are effective olefin hydrocarboxylation catalysts, are not suited for the present hydrocarboxylation of vinyl acetate, as they cause extensive production of ethylidene diesters and acetic acid. While the palladium catalysts presently utilized may in some cases have halide ligands or ions present, halides are by no means required, and there is certainly no need for the large excess of halide, as in the form of HI, CH$_3$I, and the like, characteristically employed with the halogen-promoted iridium and rhodium catalysts.

EXAMPLE 1

A 300 ml autoclave is charged with 0.110 g of [(C$_3$H$_5$)PdCl]$_2$ (0.6 mmole Pd), 3.15 g. of Ph$_3$P (12 mmole), 83 ml of acetic acid as solvent, and 37 ml of vinyl acetate (0.4 mole). The autoclave was flushed with nitrogen, pressured to 30 psig with carbon monoxide, and heated to 150° C. After reaching 150° C. one milliliter of water was pumped into the reaction solution from a Jurgenson Gauge and the pressure was raised to 700 psig with carbon monoxide. The reaction began absorbing gas as evidenced by a drop in the autoclave pressure. Therefore the autoclave pressure was maintained at 700 psig by feeding carbon monxide from a high-pressure reservoir. In addition, the water concentration in the reaction solution was maintained by addition of one milliliter of water from the Jurgenson Gauge for every 130 psig pressure drop in the high-pressure reservoir. After the addition of a total of five milliliters of water the reaction had consumed 675 psig of carbon monoxide from the high pressure reservoir. At this time the reaction was terminated. The production of α-acetoxypropionic acid was shown by a nuclear magnetic resonance and gas chromatography of the concentrated reaction solution. Pure α-acetoxypropionic acid was isolated from a subsequent fractional distillation. The mass spectrum of other fractions showed ethylidene diacetate (major), propionic acid (minor), and acrylic acid (minor) to be by-products.

EXAMPLE 2

Vinyl acetate was hydrocarboxylated in a procedure generally as described in Example 1, but employing various palladium complexes and conditions as set forth in Table 1 below along with selectivity to α-acetoxypropionic acid (α-APA).

TABLE 1

Vinyl Acetate Hydrocarboxylation with Various Palladium Complexes

[Pd]$_o$ = 0.005 M/l., [Ph$_3$P]$_o$ = 0.1M; Vinyl acetate charged = 37 ml (0.392 mole), Solvent = butyric acid (83 ml),
Temp. = 150° C., Total Press. = 700 psig, Run Time = 3 hrs.,
Water level maintained at ca. 0.9% by pumping.

| Complex | Gas Uptake (psig) | Rate (psig/min) | VA Conversion$^a$ | Selectivity$^a$ to α-APA | Portion of Reaction Solution Accounted for by GC$^c$ |
|---|---|---|---|---|---|
| [(allyl)PdCl]$_2$ | 930 | 5.9 | 96% | 67% | 97.4% |
| PdCl$_2$(Ph$_3$P)$_2$ | 310 | 1.6 | 42% | 47% | 92.9% |
| Na$_2$PdCl$_4$ | 30 | v. slow | 35% | 0% | 82.4% |
| Pd(OAc)$_2$$^d$ | 355 | 2.6 | 53% | 50% | 94.6% |
| Pd(acac)$_2$$^e$ | 350 | 2.2 | 49% | 70% | 99.3% |
| Pd(Ph$_3$P)$_4$ | 230$^b$ | 1.5 | 41% | 64% | 93.0% |

$^a$Four ml. of reaction solution removed at start of run. Conversion and selectivity results based vinyl acetate charge of 0.379 mole.
$^b$Reaction had 30 min. induction period.
$^c$Analyzed for acetaldehyde, acetic acid, vinyl acetate, propionic acid, butyric acid, and α-acetoxypropionic acid using a calibrated, internal standard GC (gas chromatography) method.
$^d$Pd (acetate)$_2$.
$^e$Pd (acetylacetonate)$_2$.

EXAMPLE 3

Hydrocarboxylations of vinyl acetate were conducted utilizing various ligands as reported in Table 2 below.

TABLE 2

Vinyl Acetate Hydrocarboxylation: Effect of Ligand

Pd Precursor = [(allyl)PdCl]$_2$, [Pd]$_o$ = 0.005 M/l., [Ligand]$_o$ = 0.1 M/l.
Vinyl acetate charged = 37 ml (0.392 mole), Solvent = butyric acid (83 ml),
Temp. = 150° C., Total Press. = 700 psig, Run Time = 3 hrs., Water Level maintained at ca. 0.9% by pumping.

| Ligand | Gas Uptake (psig) | Rate (psig/min) | VA Conversion$^a$ | Selectivity$^a$ to α-APA | Portion of Reaction Solution Accounted for by GC$^c$ |
|---|---|---|---|---|---|
| Ph$_3$P | 930 | 5.9 | 96% | 67% | 97.4% |
| (p-CH$_3$C$_6$H$_4$)$_3$P | 1040 | 11.0 | 99% | 66% | 97.7% |
| (m-CH$_3$C$_6$H$_4$)$_3$P | 930 | 6.1 | 95% | 61% | 97.8% |
| (o-CH$_3$C$_6$H$_4$)$_3$P | 0 | 0 | 21% | 0% | 96.8% |
| (p-FC$_6$H$_4$)$_3$P | 675 | 4.4 | 72% | 69% | 94.1% |
| (p-Me$_2$NC$_6$H$_4$)$_3$P | 60$^b$ | 7.8$^b$ | 28% | 11% | 96.1% |
| (NCCH$_2$CH$_2$)$_3$P | 0 | 0 | 32% | 1% | 94.8% |

$^a$Four ml. of reaction solution removed at start of run. Conversion and selectivity results based on vinyl acetate charge of 0.379 mole.
$^b$All of reaction occurred during first ten minutes.
$^c$Analyzed for acetaldehyde, acetic acid, vinyl acetate, propionic acid, butyric acid, and α-acetoxypropionic acid using a calibrated, internal standard GC(gas chromatography) method.

EXAMPLE 4

Hydrocarboxylations of vinyl acetate were conducted utilizing various temperatures, pressures and acid solvents as reported in Table 3 below.

TABLE 3

Vinyl Acetate Hydrocarboxylation: Effect of Temperature, Pressure, and Solvent

Pd Precurser = [(allyl)PdCl]$_2$, [Pd]$_o$ = 0.005 M/l., [Ph$_3$P]$_o$ = 0.1 M/l.,
Vinyl Acetate charged = 37 ml (0.392 mole), Volume of Solvent = 83 ml,
Run Time = 3 hrs., Water Level maintained at ca. 0.9% by pumping

| Temp. (°C.) | Total Press. (psig) | Solvent | Gas Uptake (psig) | Rate (psig/min) | VA Conversion$^a$ | Selectivity$^a$ to α-APA | Portion of Reaction Solution Accounted for by GC$^c$ |
|---|---|---|---|---|---|---|---|
| 130 | 700 | butyric | 80 | 0.6$^b$ | 19% | 11% | 93.4% |
| 150 | 700 | butyric | 930 | 5.9 | 96% | 67% | 97.4% |
| 170 | 700 | butyric | 780 | 5.1 | 91% | 47% | 90.4% |
| 150 | 400 | butyric | 1010 | 7.6 | 99% | 53% | 93.5% |
| 150 | 1200 | butyric | 700 | 4.6 | 84% | 61% | 95.2% |
| 150 | 700 | propionic | 940 | 6.3 | 96% | 60% | 93.6% |
| 150 | 700 | hexanoic | 980$^d$ | 4.0 | 99%$^d$ | f | f |
| 150 | 700 | acetic | 700$^e$ | 8.2 | 99%$^c$ | f | f |
| 150 | 700 | α-APA | ?$^g$ | g | 100% | g | 57.7% |

$^a$Four ml. of reaction solution removed at start of run. Conversion and selectivity results based on vinyl acetate charge of 0.379 mole.
$^b$Increased water level by 7 × after 5 hrs. Rate tripled.
$^c$Analyzed for acetaldehyde, acetic acid, vinyl acetate, propionic acid, butyric acid, and α-acetoxypropionic acid using a calibrated, internal standard GC (gas chromatography) method.
$^d$Ran for 5 hrs.
$^e$Ran for 3.4 hrs.
$^f$Did not analyze using a calibrated method.
$^g$Rate was fast initially but decreased appreciably after the first 10 min. Gas uptake was large and inexplicable. Ran for 23.7 hrs. Reaction solution was black. GC (gas chromatography) of reaction solution on SP-2401 showed a lot of high boilers, possibly lactyl lactates.

EXAMPLE 5

Vinyl acetate was carboxylated utilizing different ligand concentrations, i.e. triphenyl phosphine (Ph$_3$P), with results as reported in Table 4.

EXAMPLE 6

Hydrocarboxylations were conducted with varying water levels, with results as reported in Table 5.

TABLE 5

Vinyl Acetate Hydrocarboxylation: Effect of H$_2$O Level

Pd Precursor = [(allyl)PdCl]$_2$, [Pd]$_o$ = 0.005 m/l, [Ph$_3$P]$_o$ = 0.1M, Vinyl Acetate charged = 37 ml (0.392 moles), Solvent = butyric acid (83 ml), Temp = 150° C.,
Total Press. = 700 psig, Run time = 3 hrs., Water Level maintained at desired level by pumping.

| [H$_2$O], wt % | Gas Uptake (psig) | Rate (psig/min) | VA Conversion$^a$ | Selectivity$^a$ to α-APA | HOAc | CH$_3$CHO | Portion of Reaction Solution Accounted for by GC$^b$ |
|---|---|---|---|---|---|---|---|
| 0.9 | 930 | 5.9 | 96% | 67% | 30% | 7% | 97.4% |
| 2.5 | 850 | 6.6 | 99% | 52% | 42% | 15% | 94.0%$^c$ |
| 4.2 | 830 | 6.9 | 99% | 40% | 53% | 22% | 89.5%$^c$ |
| 8.0 | 750 | 8.6 | 100% | 29% | 65% | 27% | 87.7%$^c$ |

$^a$Four ml. of reaction solution removed at start of run. Conversion and selectivity results based on vinyl acetate charge of 0.379 mole.
$^b$Analyzed for acetaldehyde, acetic acid, vinyl acetate, propionic acid, butyric acid, and α-acetoxypropionic acid using a calibrated, internal standard GC (gas chromatography) method.
$^c$Most of the balance of the reaction solution may be water since our analysis does not include water.

EXAMPLE 7

A vinyl acetate hydrocarboxylation was conducted with determination of conversion and selectivity at specified time intervals, as reported in Table 6.

TABLE 4

Vinyl Acetate Hydrocarboxylation: Effect of Ph$_3$P Concentration

Pd Precursor = [(allyl)PdCl]$_2$, [Pd]$_o$ = 0.005 m/l, Vinyl acetate charged = 37 ml (0.392 moles),
Solvent = butyric acid (83 ml), Temp = 150° C., Total Press. = 700 psig, Run Time = 3 hrs.,
Water Level maintained at ca. 0.9% by pumping.

| [Ph$_3$P]$_o$, m/l | P/Pd | Gas Uptake (psig) | Rate (psig/min) | VA Conversion$^a$ | Selectivity$^a$ to α-APA | HOAC | HOPr | CH$_3$CHO | Portion of Reaction Solution Accounted for by GC$^b$ |
|---|---|---|---|---|---|---|---|---|---|
| 0.10 | 20:1 | 930 | 5.9 | 96% | 67% | 30% | 19% | 7% | 97.4% |
| 0.25 | 50:1 | 540 | 3.5 | 67% | 44% | 38% | 22% | 12% | 95.0% |
| 0.50 | 100:1 | 300 | 2.0 | 48% | 31% | 47% | 21% | 21% | 95.4% |

$^a$Four ml. of reaction solution removed at start of run. Conversion and selectivity results based on vinyl acetate charge of 0.379 mole.
$^b$Analyzed for acetaldehyde, acetic acid, vinyl acetate, propionic acid, butyric acid, and α-acetoxypropionic acid using a calibrated, internal standard GC (gas chromotography) method.

TABLE 6

Vinyl Acetate Hydrocarboxylation: Conversion and Selectivity vs. Time
Catalyst Charge: [(allyl)PdCl]$_2$, [Pd]$_o$ = 0.005 M/l.; [Ph$_3$P]$_o$ = 0.1 M/l.
Vinyl Acetate Charged = 37 ml (0.392 mole), Solvent = butyric acid (83 ml)
Temp. = 150° C., Total Press. = 700 psig, Water Level maintained at ca. 0.9% by pumping.

| Time (hrs) | moles/1000g. HOAc | VA | α-APA | Total | VA Conversion[a] | Selectivity[a] to α-APA | Portion of Reaction Solution Accounted for by GC[b] |
|---|---|---|---|---|---|---|---|
| Charge | 0 | 3.41 | 0 | 3.41 | — | — | 100% |
| 0 | 0 | 2.88 | 0 | 2.88 | 0 | — | 99.3% |
| 0.33 | 0.14 | 2.41 | 0.22 | 2.77 | 16% | 46% | 96.7% |
| 0.67 | 0.27 | 1.97 | 0.60 | 2.84 | 32% | 66% | 97.6% |
| 1 | 0.41 | 1.54 | 1.00 | 2.95 | 47% | 75% | 99.0% |
| 2 | 0.71 | 0.51 | 1.72 | 2.93 | 83% | 72% | 99.6% |
| 3 | 0.95 | 0.07 | 2.14 | 3.15 | 98% | 76% | 102.2% |
| 3.6 | 1.00 | 0.02 | 2.10 | 3.12 | 99% | 74% | 101.1% |

[a]Conversion and selectivity results based on vinyl acetate concentration as determined at zero time.
[b]Analyzed for acetaldehyde, acetic acid, vinyl acetate, propionic acid, butyric acid, and α-acetoxypropionic acid using a calibrated, internal standard GC method.

Vinyl propionate or other vinyl alkanoates can be substituted in the above illustrative procedures with similar results.

The hydrocarboxylation process of the present invention is generally effected in inert solvent and in accord with the procedures taught herein and also in accord with general conditions utilized for homogeneous hydrocarboxylation procedures. In general liquid carboxylic acids, for example lower alkanoic acids, have been found useful as solvents herein and those of 2 to 6 carbon atoms are particularly convenient for use. Often it is convenient to use the acid corresponding to vinyl alkanoate, e.g. acetic acid when vinyl acetate is employed, but different acids may be desirable if selectivity is thereby improved, or for other reasons. The product, e.g. α-acetoxypropionic acid, can be used as solvent, as can the molten tertiary organophosphine, although not generally preferred.

The desirability of a route from vinyl acetate to lactic acid has been discussed in a commonly assigned copending patent application of Harold Burnham Tinker, Ser. No. 581,245, filed May 27, 1975, now U.S. Pat. No. 4,072,709. However, that application concerns hydroformylation to an α-acyloxypropionaldehyde, followed by oxidation and hydrolysis to lactic acid. The present process involves hydrocarboxylation and hydrolysis reactions. The hydrolysis procedures described and illustrated in the copending application are also suitable for use in the present process and are incorporated herein by reference.

The preparation of lactic acid in accordance with the present invention involves a hydrolysis of alpha-acyloxypropionic acid to a mixture of lactic acid and carboxylic acid (this carboxylic acid will be acetic acid if vinyl acetate is the starting material for the overall process). This ester hydrolysis step may be conducted in the presence of acid or base catalysts. However it happens that the hydrolysis will also proceed at good rates in the absence of catalysts. Mineral acids, sulfonic acids and resins thereof or various acidic ion exchange resins, sodium hydroxide, potassium hydroxide, etc. can be used to increase the rate of the hydrolysis reaction. The hydrolysis can also be accomplished by heating the ester in the presence of water. The hydrolysis can be conducted at temperatures varying from say 0° C. to 300° C., and preferably from 40° C. to 220° C. Assuming that the hydrolysis is conducted as a separate step, a large excess of water will generally be used, but ratios of water to acyloxypropionic acid from 1:1 to 1000:1 or more can be used. Less than stoichiometric amounts of water can effect hydrolysis of part of an acyloxypropionic acid batch, but ordinarily sufficient water for complete hydrolysis will be used.

As taught herein, limited amounts of water are generally used for the hydrocarboxylation of vinyl acetate, in order to minimize side reactions. Ordinarily, therefore, there will not be sufficient water present to effect significant hydrolysis simultaneously with hydrocarboxylation. In this case hydrolysis of the acyloxypropionic acid is not initiated until after complete vinyl alkanoate conversion. Normally, for hydrocarboxylation catalyst recovery and recycling purposes, it may be desirable to separate the acyloxypropionic acid product, as by distillation from the reaction medium and catalyst, before diluting with water for hydrolysis. In some cases however, it is possible to carry out the hydrocarboxylation of the vinyl alkanoate and the hydrolysis of the acyloxypropionic acid produced simultaneously resulting in a one-step synthesis of lactic acid. Procedurally this involves adding additional water at a rate and as soon as feasible without undue side reactions.

Often high boiling materials are produced in the hydrocarboxylation of vinyl acetate, which may include the acid anhydride of α-acetoxypropionic acid, and lactyl lactates. Such materials can be hydrolyzed to α-acetoxypropionic acid or lactic acid, and therefore it may be appropriate to conduct the hydrolysis of such high boilers along with that of α-acetoxypropionic acid, whether in the original reaction medium or after separation therefrom.

The present invention describes a particular procedure for hydrocarboxylating vinyl alkanoates to α-acyloxypropionic acid, and hydrolysis to lactic acid. However other procedures if found effective for such hydrocarboxylation with good selectivity, are visualized as also suitable for a process of converting vinyl alkanoates to lactic acid.

EXAMPLE 8

Lactic acid was synthesized in a 300 ml autoclave by the hydrolysis of α-acetoxypropionic acid (66 grams, 500 mmoles) in water (150 ml) at 150° C. Acetic acid and most of the water were removed by distillation.

EXAMPLE 9

α-acetoxypropionic acid (33 grams, 250 mmoles) was dissolved in water (150 ml). The solution was charged to an autoclave and heated to 200° C. Acetic acid and water were removed by distillation to give lactic acid.

EXAMPLE 10

A 300 ml autoclave is charged with 0.692 g. of Pd(Ph$_3$P)$_4$ (0.6 mmole Pd), 3.15 g. of Ph$_3$P (12 mmole), 83 ml of butyric acid as solvent, and 37 ml of vinyl acetate (0.4 mole). The autoclave was flushed, heated-up, and operated in a procedure similar to that described in Example 1. Several 1-ml increments of water were added, and then additional water to make a total of 9 ml. was added and the reaction continued overnight. After 23 hours of reaction time at 150° C. and 700 psig the reaction was terminated and analyzed by gas chromatography. The product mixture contained both 60-acetoxypropionic and lactic acids, the amount of lactic acid being 67–100% of the α-acetoxypropionic acid. The presence of lactic acid in this mixture was confirmed by nuclear magnetic resonance and mass spectroscopy. Thus lactic acid was produced in this experiment in one-step from vinyl acetate.

The hydrocarboxylations herein of vinyl alkanoates, e.g. vinyl acetate, over a tertiary organophosphine stabilized palladium catalyst result in high selectivity and conversion to α-acyloxypropionic acid, e.g. up to 60 or 70% or more based on vinyl acetate, and this is achievable with high conversions. Moreover it may well be possible to improve the selectivity by hydrolyzing some of the high boilers generally produced. This, together with the efficient and convenient hydrolysis step, makes the procedure a very promising route to lactic acid.

What is claimed is:

1. A process for the hydrocarboxylation of vinyl alkanoates to produce α-acyloxypropionic acid which comprises contacting the vinyl alkanoates with carbon monoxide and water in a liquid reaction medium comprising a low concentration, no greater than about 3% by weight, of water and a catalyst containing palladium and tertiary organophosphine, and excess tertiary organophosphine.

2. The process of claim 1 in which a temperature of 100° to 200° C. is employed.

3. The process of claim 2 in which a pressure of 100 to 1000 psi is employed.

4. The process of claim 1 in which a phosphine with aromatic groups attached to the phosphorus is employed.

5. The process of claim 4 in which triphenylphosphine is employed.

6. The process of claim 1 in which tri-arylphosphine is employed in which aryl is selected from meta- or para-tolyl.

7. The process of claim 1 in which the vinyl alkanoate is vinyl acetate and it produces α-acetoxypropionic acid.

8. The process of claim 7 in which phosphine ligand is present in molar ratio to palladium in the range of about 10:1 to about 100:1.

9. The process of claim 7 in which the water concentration is maintained at a low level close to 1% by weight of the reaction medium.

10. The process of claim 7 in which a carboxylic acid solvent is employed.

11. The process of claim 7 in which the solvent is selected from acetic, propionic or butyric acid.

12. The process of claim 7 in which the temperature employed is no greater than 170° C.

13. A process of hydrocarboxylating vinyl alkanoates which comprises reacting vinyl alkanoates with carbon monoxide and water in a liquid reaction medium with a tertiary organophosphine stabilized palladium catalyst in which the water is present in a very small amount much less than stoichiometric and additional water is added during the reaction to replace that reacted.

14. The process of claim 13 in which the vinyl alkanoate is vinyl acetate and the water is added at approximately the reaction rate as determined by monitoring the carbon monoxide consumption.

15. A process of preparing lactic acid which comprises hydrocarboxylating vinyl alkanoates in accord with the process of claim 1 and hydrolyzing the α-acyloxypropionic acid to lactic acid.

16. The process of claim 15 in which the hydrolysis is accomplished by heating with water.

17. The process of claim 15 in which the vinyl alkanoate is vinyl acetate.

18. A process of preparing lactic acid in one step which comprises hydrocarboxylating vinyl alkanoates in accord with the process of claim 1 with the simultaneous hydrolysis of the α-acyloxypropionic acid produced.

* * * * *